US00PP13472P3

(12) United States Plant Patent
Herrington et al.

(10) Patent No.: US PP13,472 P3
(45) Date of Patent: Jan. 14, 2003

(54) 'LITTLE PHILLIP NO. 1' BERMUDA GRASS

(75) Inventors: Larry Herrington, Florien, LA (US); Clyde Sneed, Many, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/855,065

(22) Filed: May 14, 2001

(65) Prior Publication Data

US 2002/0194666 P1 Dec. 19, 2002

(51) Int. Cl.[7] ..... A01H 5/00

(52) U.S. Cl. ..... Plt./389

(58) Field of Search ..... Plt./389

*Primary Examiner*—Bruce R. Campell
*Assistant Examiner*—Annette Para
(74) *Attorney, Agent, or Firm*—André J. Porter; John H. Runnels; Bonnie J. Davis

(57) ABSTRACT

An improved bermudagrass plant named 'Little Phillip No. 1' is disclosed having superior properties. 'Little Phillip No. 1' is characterized by its moderate stem size, reduced rate of leaf senescence, and superior forage production.

3 Drawing Sheets

This invention pertains to a new and distinct variety of hybrid bermudagrass which has superior forage production, spring growth, and early stolon development.

GENUS AND SPECIES NAME

This new and distinct variety is a naturally-occurring, vegetatively propagated variety of hybrid bermudagrass, *Cynodon dactylon* (L.) Pers., which demonstrates superior forage production, spring growth, and early stolon development over other available hybrid bermudagrass varieties.

VARIETY DENOMINATION

This new and distinct variety is identified as 'Little Phillip No. 1,' and is characterized by its moderate stem size, reduced rate of leaf senescence, and superior forage production.

BRIEF DESRIPTION OF THE DRAWINGS

'Little Phillip No. 1' was discoverd in a cultivated hay field of 'Alicia' bermudagrass (unpatented) on a farm owned by Clyde Sneed, located near Many, La. (911 address: 3271 Corleyville Road, Many, La. 71449) (West Louisiana Coastal Plain area). 'Little Phillip No. 1' was initially observed by Clyde Sneed in a 10 acre field of 'Alicia' as two small inclusions occupying an area of about 4–5 $ft^2$. During the next five years 'Little Phillip No. 1' vigorously spread into areas previously occupied by 'Alicia.' 'Little Phillip No. 1' now occupies about 2 acres of the 10 acre field, since it has out-competed 'Alicia.' The novel burmudagrass is suitable for use in farming areas for hay fields, erosion control, and pastures.

In September 1996, 'Little Phillip No. 1' was asexually reproduced by vegetative propagation for experimental purposes. To asexually reproduce 'Little Phillip No. 1, ' stolon samples were transferred by Larry Herrington to two small plots (approximately ¼ of an acre each) at two separate locations: Clyde Sneed's farm, located in Corleyville Road, Many, La.; and a neighboring farm owned by Larry Herrington, located in Zachary Lane, Florien, La. These sites were plowed and weed-free before transfer of the vegetative planting material. Approximately one month after planting the samples, the sites were mowed to control weed competition. In the winter of 1996–1997, broiler litter (about 1 ton per acre) was applied to the sites as a fertilizer. Both sites were sprayed with the herbicide 2,4-D around April 1997 to control broad-leaf weeds. During that period, the vigorous establishment and impressive growth of 'Little Phillip No. 1' was particularly apparent. The newly grown plant stands remained true to type after being asexually reproduced.

It is believed that 'Little Phillip No. 1' most likely originally developed from a seed, and that 'Alicia' is probably at least one of the parents of 'Little Phillip No. 1.' 'Little Phillip No. 1' is presumed to be either a natural hybrid between 'Alicia' and another bermudagrass (common bermudagrass is widely distributed in the area) or the outcome of a self-fertilized seed of 'Alicia' (which rarely produces fertile seed). ('Little Phillip No. 1' could be the result of a mutation, or of a natural recombination of 'Alicia' genes.)

Figure 1:
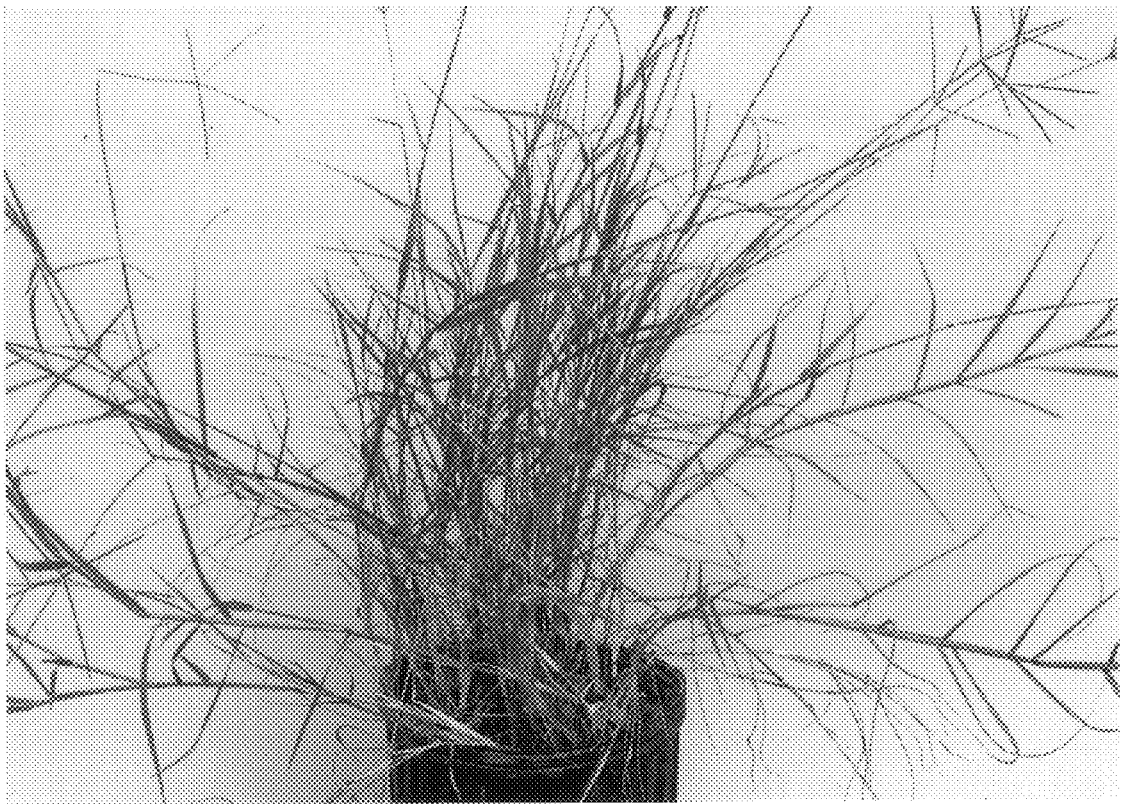
FIG. 1 is a color photograph depicting the growth form of the new and distinct variety of bermudagrass identified as 'Little Phillip No. 1.'

FIG. 1 depicts the growth form of the above ground vegetative growth of 'Little Phillip No. 1.' Generally, 'Little Phillip No. 1' is similar in appearance to other robust hybrid bermudagrass varieties. It is a stoloniferous and rhizomatous perennial grass, and typically forms a moderately dense sod with vegetative growth attaining a height of about 1 ft.

Figure 2:
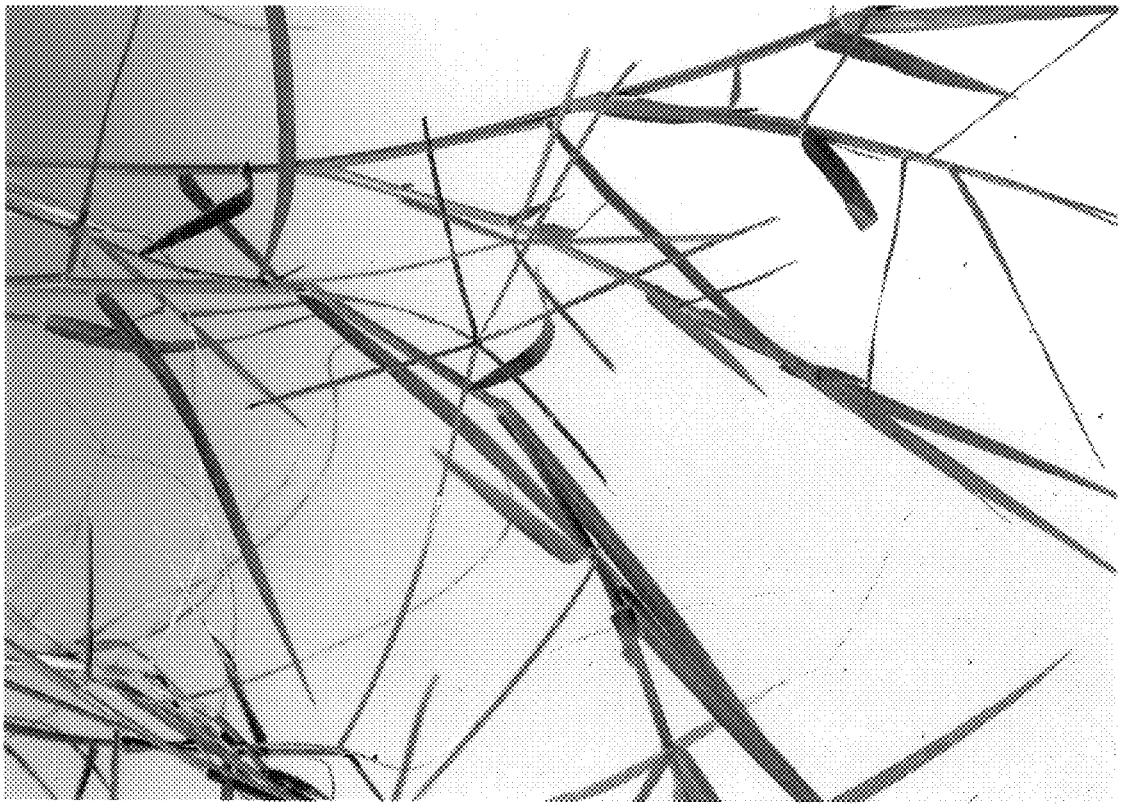
FIG. 2 is a color photograph depicting prostrate stolons and leaf blades of 'Little Phillip No. 1.'

FIG. 2 depicts prostrate stolons and leaf blades of 'Little Phillip No. 1.' By the eighth week of growth, the prostrate stolons are typically average 2.0 mm in width, while upright flowering stems average 1.5 mm in width. (During the same eight-week growth period, stolons of 'Alicia' typically average 1.5 mm in width, while upright flowering stems average 0.75 mm in width.) Stolons typically reach more than 1 m (several feet) in length. Leaf sheaths encircle the stems and are glabrous except for tufts of hair on either side of the collar extending into the ligular area. The ligule is a narrow, ciliate membrane which combines with the collar to produce a readily discernible band between the sheath and leaf blade. Leaf blades are generally linear, flat to slightly folded, and glabrous with only the mid-vein readily discernible. Leaf blades are generally from 3–6 mm wide with most leaf lengths ranging from 50–100 mm. Leaf margins are typically smooth. The upper surface of the leaf blade is slightly scabrous.

Figure 3:
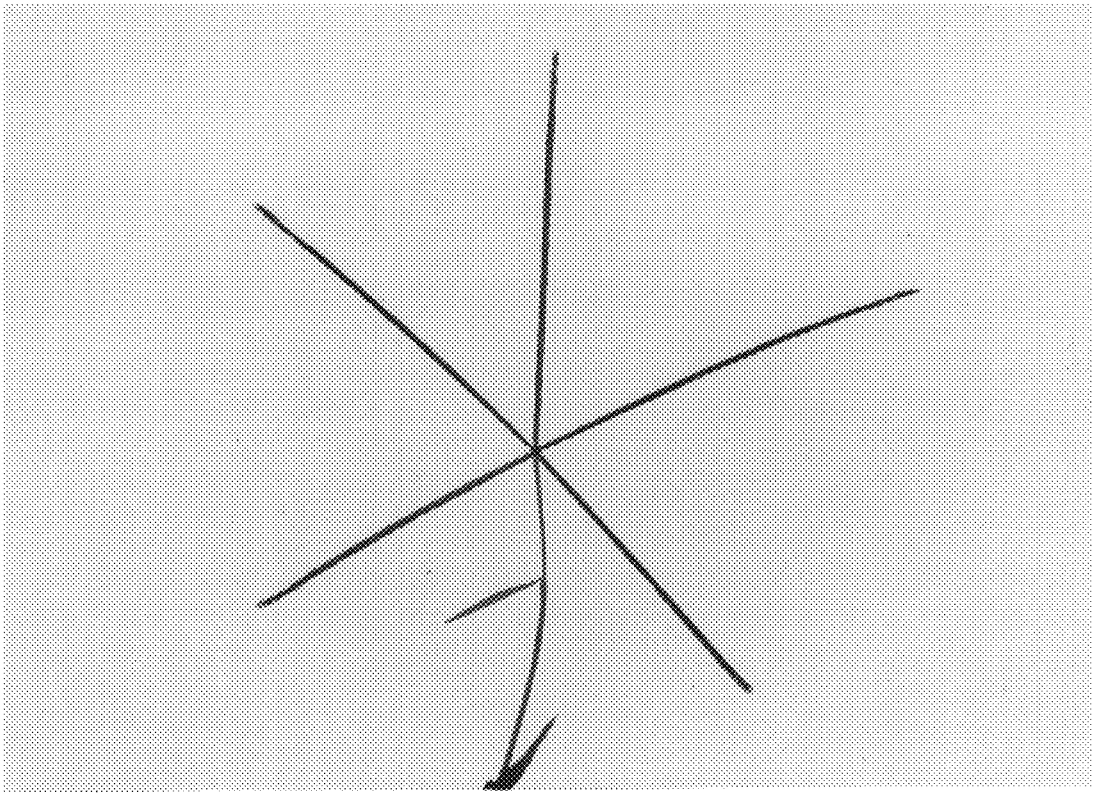
FIG. 3 is a color photograph depicting a seedhead from 'Little Phillip No. 1.'

FIG. 3 depicts a seedhead from 'Little Phillip No. 1.' Seedheads (inflorescences) may extend up to about 18 inches in height. These inflorescences comprise digitate, spicate branches, which can have from four to eight branches; however, inflorescences having from five to seven branches typically occur most frequently. The branches are about 6–7.5 cm long, and comprise a narrow scabrous rachis with numerous awnless spikelets. These spikelets are typically flattened and compressed along one side of the rachis. Spikelets are about 3 mm long and contain a single floret each. Although flowering can be profuse, no seed production has been observed.

Tests Conducted

To confirm that 'Little Phillip No. 1' was a new and distinct variety of bermudagrass capable of true vegetative (asexual) reproduction, in October of 1996 about 10 to 12 stolon samples from 'Little Phillip No. 1,' having lengths between 18 and 24 inches, were planted for asexual reproduction at the Louisiana Agricultural Experiment Station (Rosepine Research Station), located in Rosepine, La. Comparisons of forage production were made with leading bermudagrass varieties. Three vegetatively propagated bermudagrass varieties, 'Russell,' 'Tifton-85,' and 'Jiggs' (all unpatented varieties) were selected to conduct comparison tests with 'Little Phillip No. 1.' These three varieties were chosen because they represent superior commercially available bermudagrass varieties in the West Louisiana Coastal Plain area, and naturally provide a range in growth type among varieties.

Established stands of each grass were evaluated in field plot clipping trials for forage production and stand survival. Each grass entry was planted in individual plots having dimensions of 7 ft×20 ft, using a Bowie fine sandy loam soil. The plots were placed 5 ft apart. At the beginning of each growing season (1998 to 2000), each plot was fertilized with 50 pounds per acre of nitrogen, $P_2O_5$, and $K_2O$ (about 300 pounds per acre of 16% N, 16% $P_2O_5$, and 16% $K_2O$ (16-16-16 mixed fertilizer)). After each forage harvest, with the exception of the last harvest of each year, 50 pounds per acre of nitrogen was again applied to the soil in each plot. Harvests were made throughout the 1998 to 2000 growing seasons. Tests were conducted on forage yield samples to determine the dry matter percentage. Also, crude protein and in vitro digestibility analyses were conducted. The results of these tests confirmed that vigorous vegetative propagation (asexual reproduction) resulted from planting stolons of 'Little Phillip No. 1.' The vegetatively propagated plant remained true to type, exhibiting all of the morphological characteristics of the original plant.

Forage dry matter yields of the hybrid bermudagrass varieties for the 1998 growing season are shown in Table 1.

TABLE 1

| Variety | Harvest date | | | | |
|---|---|---|---|---|---|
| | May 11 | June 18 | July 21 | Aug. 28 | Oct. 21 |
| | pounds per acre | | | | |
| 'Russell' | 870 | 1010 | 630 | 1590 | 2570 |
| 'Jiggs' | 730 | 1160 | 530 | 2620 | 3290 |
| 'Tifton-85' | 480 | 1400 | 770 | 2710 | 2610 |
| 'Little Phillip No. 1' | 1410 | 1070 | 680 | 3680 | 3000 |

Forage dry matter yields of the hybrid bermudagrass varieties for the 1999 growing season are shown in Table 2. Forage production was more uniformly distributed throughout this growing season than the 1998 growing season, probably due primarily to more uniform rainfall through the growing season.

TABLE 2

| Variety | Harvest date | | | | |
|---|---|---|---|---|---|
| | May 19 | June 16 | July 16 | Aug. 30 | Nov. 3 |
| | pounds per acre | | | | |
| 'Russell' | 1020 | 1690 | 1650 | 1210 | 770 |
| 'Jiggs' | 1260 | 2420 | 2760 | 2520 | 2180 |
| 'Tifton-85' | 1160 | 2570 | 2810 | 2710 | 2230 |
| 'Little Phillip No. 1' | 2860 | 2950 | 3530 | 4360 | 3240 |

Forage dry matter yields of the hybrid bermudagrass varieties for the 2000 growing season are shown in Table 3. Yields were less uniform in 2000 than previous years, probably due primarily to low soil moisture.

TABLE 3

| Variety | Harvest date | | | | |
|---|---|---|---|---|---|
| | May 3 | June 5 | July 13 | Sept. 15 | Oct. 26 |
| | pounds per acre | | | | |
| 'Russell' | 1470 | 1990 | 2100 | 820 | 660 |
| 'Jiggs' | 2090 | 2930 | 4040 | 1580 | 1260 |
| 'Tifton-85' | 1680 | 2920 | 3450 | 1670 | 840 |
| 'Little Phillip No. 1' | 3210 | 3990 | 3720 | 2920 | 1970 |

Three-year average dry matter yields of the hybrid bermudagrass varieties for the 1998, 1999 and 2000 growing seasons are shown in Table 4. Total forage production for 'Tifton-85' and 'Jiggs' was over 9,000 pounds per acre; however, the forage yield of 'Little Phillip No. 1' was at least 30% more than 'Tifton-85' and 'Jiggs,' and twice that of 'Russell' during the three-year period.

TABLE 4

| Variety | Forage yield pounds per acre per year |
|---|---|
| 'Russell' | 6250 a† |
| 'Jiggs' | 9800 b |
| 'Tifton-85' | 9350 b |
| 'Little Phillip No. 1' | 13310 c |

†Average yields of varieties followed by a common letter do not differ ($P > 0.05$) according to Duncan's Multiple Range Test.

Crude protein and in vitro digestibility of the grass varieties for the 1998 and 1999 growing seasons are shown in Table 5. Crude protein did not differ significantly among the varieties. In vitro digestibility, however, was higher in 1998 than in 1999. (Such differences are typical and reflect variations in growing conditions.)

TABLE 5

| Variety | Crude protein† | In vitro digestibility 1998 | In vitro digestibility 1999 |
|---|---|---|---|
| | % | | |
| 'Russell' | 13.8 | 60.2 c‡ | 57.6 a |
| 'Jiggs' | 13.8 | 62.6 b | 57.8 a |
| 'Tifton-85' | 14.0 | 64.5 a | 57.6 a |
| 'Little Phillip No. 1' | 14.1 | 62.8 b | 57.9 a |

†Varieties did not differ significantly (P > 0.05) in crude protein concentration in either year.
‡Responses among varieties in in vitro digestibility differed between years. Average digestibility values for varieties within each year do not differ (P > 0.05) if followed by a common letter.

Production of 'Tifton-85' at the first harvest was comparatively low because of its open stand which naturally occurs early in each growing season. ('Tifton-85' naturally produces a sparse or open stand with bare soil available for competing plants early in the growing season and after each harvest.)

Distinguishing Morphological Features of 'Little Phillip No. 1'

To assess some of the morphological features of 'Little Phillip No. 1,' measurements of leaf blade length and width were taken of the uppermost fully expanded leaf of the vegetative tillers of all four bermudagrass varieties, as shown in Table 6. The measurements were taken from new regrowth on May 8, 2001, five days after a forage harvest. Five tillers in each of four replicates of each of the bermudagrass varieties were measured. Leaf measurements were subjected to statistical analysis using analysis of variance with significantly different responses (P<0.05) assessed by least significant difference procedures.

TABLE 6

| Variety | Leaf width (mm) | Leaf length (mm) |
|---|---|---|
| 'Tifton-85' | 4.7 a† | 75.3 a |
| 'Little Phillip No. 1' | 4.3 ab | 79.7 a |
| 'Jiggs' | 4.1 b | 75.2 a |
| 'Russell' | 3.3 c | 59.3 b |
| Least significant difference | 0.46 | 12.2 |

†Measurements within a column followed by a common letter do not differ (P < 0.05) by the least significant difference procedure.

As shown in Table 6, 'Little Phillip No. 1' and 'Tifton-85' had similar leaf blade dimensions. However, 'Little Phillip No. 1' can be distinguished from 'Tifton-85' by its dense, closed sod under comparable growing conditions. Another distinguishing feature is that 'Little Phillip No. 1' has a larger number of leaves per unit of area than 'Tifton-85.' Additionally, 'Tifton-85' stands are more vulnerable to invasion by other plants (e.g., common bermudagrass), than 'Little Phillip No. 1.' 'Tifton-85' stands tend to grow upright with a substantial amount of bare ground exposed following defoliation. However, 'Little Phillip No. 1' develops stands with more closely spaced plants that are not as readily invaded by other plants, especially during the period immediately following harvest of the forage growth.

'Little Phillip No. 1' and 'Jiggs' also had similar leaf blade dimensions, as shown in Table 6.

'Little Phillip No. 1' had longer and wider leaf blades than 'Russell,' as shown in Table 6. 'Little Phillip No. 1' can also be distinguished from 'Russell' by its larger stem size.

Under comparable growing conditions, 'Little Phillip No. 1' was found to exhibit greater rates of vegetative growth and stolon development than 'Russell,' 'Jiggs' and 'Tifton-85.' Additionally, 'Little Phillip No. 1' exhibited a faster rate of plant morphological development than 'Russell,' and 'Tifton-85.'

'Little Phillip No. 1' Distinguished From Alicia

Under comparable growing conditions, 'Little Phillip No. 1' can be distinguished from Alicia by its larger stem size and reduced rate of leaf senescence in the lower canopy layer of stands. The senescence of the lower leaves in 'Alicia' causes deterioration of forage quality after about four weeks or more of growth. Since the rate of senescence in 'Little Phillip No. 1' is substantially less than the rate of senescence in 'Alicia,' forage of a higher quality is produced by 'Little Phillip No. 1' throughout the canopy for forage of 6 or more weeks of age, depending on growing conditions.

Several additional experiments will be conducted by the Louisiana Agricultural Experiment Station, including evaluations of forage yield and quality in response to the length of growing periods between harvests and response to nitrogen fertilizer rate. Also, comparisons of forage yield and quality with currently used varieties will be made at various locations in Louisiana.

We claim:

1. A bermudagrass plant substantially as described and illustrated in the specification herein.

* * * * *